US00PP16393P2

(12) United States Plant Patent
Hofmann

(10) Patent No.: US PP16,393 P2
(45) Date of Patent: Mar. 28, 2006

(54) ***OENOTHERA* PLANT NAMED 'INNOENO131'**

(50) Latin Name: *Oenothera hybrida*
Varietal Denomination: INNOENO131

(75) Inventor: Silvia Hofmann, Mainz (DE)

(73) Assignee: InnovaPlant GmbH & Company KG, Gensingen (DE)

( * ) Notice: Subject to any disclaimer, the term of this patent is extended or adjusted under 35 U.S.C. 154(b) by 95 days.

(21) Appl. No.: 10/959,827

(22) Filed: Oct. 6, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Oenothera* plant named 'INNOENO131', characterized by its compact and outwardly spreading plant habit; vigorous and freely branching growth habit; freely and early flowering habit; long flowering period; and large bright yellow-colored flowers.

1 Drawing Sheet

Botanical classification/cultivar designation: *Oenothera hybrida* cultivar INNOENO131.

BACKGROUND OF THE INVENTION

The present Invention relates to a new and distinct cultivar of *Oenothera* plant, botanically known as *Oenothera hybrida,* and hereinafter referred to by the cultivar name INNOENO131.

The new *Oenothera* is a product of a planned breeding program conducted by the Inventor in Gensingen, Germany. The objective of the breeding program is to create new compact and freely-branching *Oenotheras* with numerous flowers and attractive flower coloration.

The new *Oenothera* originated from a cross-pollination made by the Inventor during the summer of 1999 of the *Oenothera hybrida* cultivar African Sun, not patented, as the female, or seed, parent with the *Oenothera hybrida* cultivar Narrow Gray Leaved, not patented, as the male, or pollen, parent. The new *Oenothera* was selected as a single plant from the resulting progeny of the cross-pollination by the Inventor during the summer of 2000 in an controlled environment in Gensingen, Germany.

Asexual reproduction of the new cultivar by terminal cuttings in a controlled environment in Gensingen, Germany since the summer of 2001, has shown that the unique features of this new *Oenothera* are stable and reproduced true to type in successive generations.

SUMMARY OF THE INVENTION

Plants of the cultivar INNOENO131 have not been observed under all possible environmental conditions. The phenotype may vary somewhat with variations in environment such as temperature and light intensity without, however, any variance in genotype.

The following traits have been repeatedly observed and are determined to be the unique characteristics of 'INNOENO131'. These characteristics in combination distinguish 'INNOENO131' as a new and distinct cultivar of *Oenothera:*

1. Compact and outwardly spreading plant habit.
2. Vigorous and freely branching growth habit.
3. Freely and early flowering habit.
4. Long flowering period.
5. Large bright yellow-colored flowers.

Plants of the new *Oenothera* are most similar to plants of the female parent, the cultivar African Sun. In side-by-side comparisons conducted in Gensingen, Germany, plants of the new *Oenothera* differed from plants of the cultivar African Sun in the following characteristics:

1. Plants of the new *Oenothera* flowered earlier than plants of the cultivar African Sun.
2. Plants of the new *Oenothera* had larger flowers than plants of the cultivar African Sun.

Plants of the new *Oenothera* can also be compared to of the male parent, the cultivar Narrow Gray Leaved. In side-by-side comparisons conducted in Gensingen, Germany, plants of the new *Oenothera* differed from plants of the cultivar Narrow Gray Leaved in the following characteristics:

1. Plants of the new *Oenothera* were more outwardly spreading than and not as upright as plants of the cultivar Narrow Gray Leaved.
2. Flower color of plants of the new *Oenothera* was more intense than flower color of plants of the cultivar Narrow Gray Leaved.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Oenothera.*

The photograph at the top of the sheet is a close-up view of typical flowers of 'INNOENO131'.

The photograph at the bottom of the sheet comprises a side perspective view of a typical flowering plant of 'INNOENO131' grown in a container.

DETAILED BOTANICAL DESCRIPTION

The aforementioned photographs and following observations and measurements describe plants grown in Bonsall, Calif. in an outdoor nursery during the late spring with day temperatures ranging from 18 to 38° C. and night temperatures ranging from 10 to 18° C. Plants were grown in 12.5-cm container and had been growing for about seven weeks when the photographs and description were taken. Plants were pinched one time. Color references are made to The Royal Horticultural Society Colour Chart, 1995 Edition, except where general terms of ordinary dictionary significance are used.

Botanical classification: *Oenothera hybrida* cultivar INNOENO131.

Parentage:

*Female parent.*—*Oenothera hybrida* cultivar African Sun, not patented.

*Male parent.*—*Oenothera hybrida* cultivar Narrow Grey Leaved, not patented.

Propagation:

*Type cutting.*—Vegetative cuttings.

*Time to initiate roots, summer.*—About 14 days at 20° C.

*Time to initiate roots, winter.*—About 18 days at 20° C.

*Time to produce a rooted young plant, summer and winter.*—About 20 days at 20° C.

*Root description.*—Fine; freely branching; white in color.

Plant description:

*Form.*—Compact and outwardly spreading plant habit; low-mounding. Freely branching growth habit with about eight lateral branches per plant. Vigorous growth habit.

*Plant height.*—About 17 cm.

*Plant diameter.*—About 37 cm.

*Lateral branches.*—Length: About 24 cm. Diameter: About 5 mm. Internode length: About 1 cm. Strength: Fair. Texture: Fine pubescence. Color, young stems: 145C. Color, older stems: 177C.

*Foliage description.*—Arrangement: Alternate; simple. Length: About 4.5 cm. Width: About 6 mm. Shape: Narrowly elliptic. Apex: Acute. Base: Attenuate. Margin: Entire. Texture, upper and lower surfaces: Fine pubescence. Venation pattern: Pinnate; arcuate. Color: Developing and fully expanded foliage, upper surface: 147A. Developing and fully expanded foliage, lower surface: 147B. Venation, upper and lower surfaces: 147B. Petiole: Length: About 8 mm. Diameter: About 1 mm. Texture, upper and lower surfaces: Smooth. Color, upper and lower surfaces: 146B.

Flower description:

*Flower type and habit.*—Solitary terminal and axillary rounded flowers. Flowers persistent. Flowers face upright or outwardly.

*Quantity.*—Freely flowering; about 24 flower buds and open flowers per lateral branch.

*Natural flowering season.*—Long flowering period; plants typically flower from June though October in Southern California; flowering continuous during this period. Plants start flowering about four weeks after planting.

*Flower longevity on the plant.*—About one to two days.

*Fragrance.*—Not detected.

*Flower size.*—Length: About 5 cm. Width: About 5 cm. Depth: About 4.5 cm.

*Flower buds.*—Length: About 1.5 cm. Diameter: About 4 mm. Shape: Slender, elongated. Color: 144A to 144B.

*Petals.*—Quantity/arrangement: Four petals in a single whorl; fused at base. Length: About 2.5 cm. Width: About 1.7 cm. Shape: Elongated cordate. Apex: Emarginate. Margin: Entire. Texture, upper and lower surfaces: Smooth, satiny. Color: When opening, upper and lower surfaces: 7A. Fully opened, upper and lower surfaces: 7B.

*Sepals.*—Arrangement/appearance: Single whorl of four sepals; fused at the base. Length: About 1.5 cm. Width: About 2.5 mm. Shape: Narrowly elliptic. Apex: Acute. Base: Fused. Margin: Entire. Texture, upper surface: Smooth. Texture, lower surface: Fine pubescence. Color, upper surface: 3B. Color, lower surface: 144C to 144D.

*Peduncles.*—Length: About 8 mm. Width: About 1 mm. Angle: About 30° from stem axis. Strength: Strong. Texture: Pubescent. Color: 144C.

*Reproductive organs.*—Stamens: Quantity per flower: Eight. Anther shape: Linear; slender. Anther length: About 4 mm. Anther diameter: Less than 1 mm. Anther color: 163C. Pollen amount: Moderate. Pollen color: 1A. Pistils: Quantity per flower: One. Pistil length: About 3 cm. Style length: About 2.2 mm. Style color: 12A. Stigma shape: Four-parted. Stigma color: 12A. Ovary color: 146B.

*Fruit/seed.*—Fruit and seed production has not been observed.

Disease/pest resistance: Plants of the new *Oenothera* have not been noted to be resistant to pathogens or pests common to *Oenothera*.

Temperature tolerance: Plants of the new *Oenothera* have been observed to tolerate temperatures from 6 to 40° C.

It is claimed:

1. A new and distinct cultivar of *Oenothera* plant named 'INNOENO131', as illustrated and described.

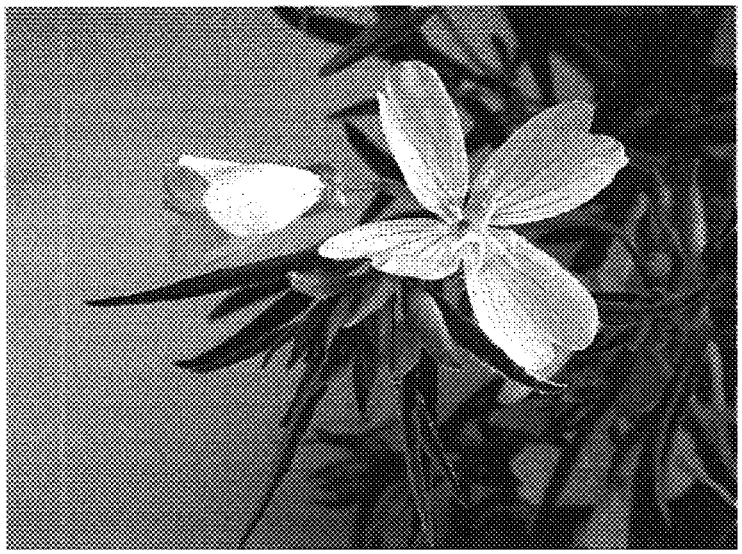
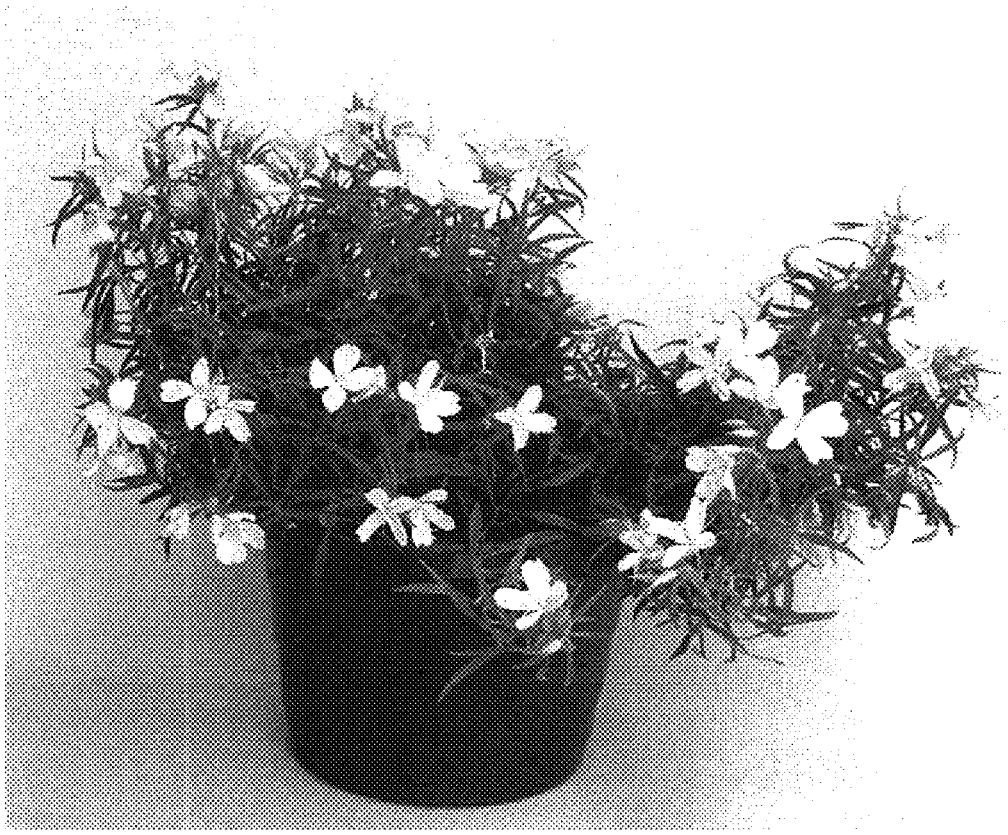

* * * * *